US006379888B1

(12) United States Patent
Nadeau et al.

(10) Patent No.: US 6,379,888 B1
(45) Date of Patent: Apr. 30, 2002

(54) UNIVERSAL PROBES AND METHODS FOR DETECTION OF NUCLEIC ACIDS

(75) Inventors: James G. Nadeau, Chapel Hill; C. Preston Linn; J. Bruce Pitner, both of Durham; Cheryl H. Dean, Raleigh; G. Terrance Walker, Chapel Hill, all of NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/406,074

(22) Filed: Sep. 27, 1999

(51) Int. Cl.[7] .......................... C12Q 1/68; C12P 19/34; C07H 21/04; C07H 21/02; G01N 33/00
(52) U.S. Cl. .......................... 435/6; 435/91.2; 435/94; 436/94; 536/24.3; 536/23.1; 935/78
(58) Field of Search .......................... 435/6, 91.2, 94; 536/24.3, 23.1; 436/94; 935/78

(56) References Cited

U.S. PATENT DOCUMENTS

| 5,270,184 | A | 12/1993 | Walker et al. |
| 5,348,853 | A | 9/1994 | Wang et al. |
| 5,455,166 | A | 10/1995 | Walker |
| 5,547,861 | A | 8/1996 | Nadeau et al. |
| 5,550,025 | A | 8/1996 | Walker |
| 5,593,867 | A | 1/1997 | Walker et al. |
| 5,607,834 | A | 3/1997 | Bagwell |
| 5,691,145 | A | 11/1997 | Pitner et al. |
| 5,866,336 | A | 2/1999 | Nazarenko et al. |
| 5,935,791 | A | 8/1999 | Nadeau et al. |
| 6,130,047 | A | * 10/2000 | Nadeau et al. .................. 435/6 |

FOREIGN PATENT DOCUMENTS

| EP | 0 684 315 A1 | 3/1995 |
| EP | 0 878 554 A2 | 11/1998 |
| EP | 0 881 302 A2 | 12/1998 |
| JP | 93015439 B | 3/1993 |

OTHER PUBLICATIONS

M.S. Ellwood et al., Clin. Chem. 32/9, 1631–1636 (1986), Strand Displacement Applied to Assays with Nucleic Acid Probes.

* cited by examiner

Primary Examiner—W. Gary Jones
Assistant Examiner—Arun Chakrabarti
(74) Attorney, Agent, or Firm—Donna R. Fugit; David W. Highet (57) ABSTRACT

Signal primers are employed for detection of nucleic acid target sequences by fluorescence quenching mechanisms. The signal primer comprises a first and a second oligonucleotide and is partially single-stranded and partially double-stranded. In the presence of target, the second oligonucleotide of the signal primer is displaced from the first and a conformational change in a reporter probe occurs which changes the distance between the members of a donor/quencher dye pair linked to the reporter probe. The change in proximity between the dyes causes an increase or a decrease in fluorescence quenching, which is detected as an indication of the presence of the target sequence.

37 Claims, 4 Drawing Sheets

UNIVERSAL PROBES AND METHODS FOR DETECTION OF NUCLEIC ACIDS

FIELD OF THE INVENTION

The invention relates to materials and methods for detecting nucleic acid target sequences.

BACKGROUND OF THE INVENTION

Sequence-specific hybridization of labeled oligonucleotide probes has long been used as a means for detecting and identifying selected nucleotide sequences, and labeling of such probes with fluorescent labels has provided a relatively sensitive, nonradioactive means for facilitating detection of probe hybridization. Recently developed detection methods employ the process of fluorescence energy transfer (FET) rather than direct detection of fluorescence intensity for detection of probe hybridization. Fluorescence energy transfer occurs between a donor fluorophore and a quencher dye (which may or may not be a fluorophore) when the absorption spectrum of one (the quencher) overlaps the emission spectrum of the other (the donor) and the two dyes are in close proximity. Dyes with these properties are referred to as donor/quencher dye pairs or energy transfer dye pairs. The excited-state energy of the donor fluorophore is transferred by a resonance dipole-induced dipole interaction to the neighboring quencher. This results in quenching of donor fluorescence. In some cases, if the quencher is also a fluorophore, the intensity of its fluorescence may be enhanced. The efficiency of energy transfer is highly dependent on the distance between the donor and quencher, and equations predicting these relationships have been developed by Förster (1948. *Ann. Phys.* 2, 55–75). The distance between donor and quencher dyes at which energy transfer efficiency is 50% is referred to as the Förster distance ($R_O$). Other mechanisms of fluorescence quenching are also known including, for example, charge transfer and collisional quenching.

Energy transfer and other mechanisms which rely on the interaction of two dyes in close proximity to produce quenching are an attractive means for detecting or identifying nucleotide sequences, as such assays may be conducted in homogeneous formats. Homogeneous assay formats are simpler than conventional probe hybridization assays which rely on detection of the fluorescence of a single fluorophore label, as heterogeneous assays generally require additional steps to separate hybridized label from free label. Typically, FET and related methods have relied upon monitoring a change in the fluorescence properties of one or both dye labels when they are brought together by the hybridization of two complementary oligonucleotides. In this format, the change in fluorescence properties may be measured as a change in the amount of energy transfer or as a change in the amount of fluorescence quenching, typically indicated as an increase in the fluorescence intensity of one of the dyes. In this way, the nucleotide sequence of interest may be detected without separation of unhybridized and hybridized oligonucleotides. The hybridization may occur between two separate complementary oligonucleotides, one of which is labeled with the donor fluorophore and one of which is labeled with the quencher. In double-stranded form there is decreased donor fluorescence (increased quenching) and/or increased energy transfer as compared to the single-stranded oligonucleotides. Several formats for FET hybridization assays are reviewed in *Nonisotopic DNA Probe Techniques* (1992. Academic Press, Inc., pgs. 311–352). Alternatively, the donor and quencher may be linked to a single oligonucleotide such that there is a detectable difference in the fluorescence properties of one or both when the oligonucleotide is unhybridized vs. when it is hybridized to its complementary sequence. In this format, donor fluorescence is typically increased and energy transfer/quenching are decreased when the oligonucleotide is hybridized. For example, a self-complementary oligonucleotide labeled at each end may form a hairpin which brings the two fluorophores (i.e., the 5' and 3' ends) into close spatial proximity where energy transfer and quenching can occur. Hybridization of the self-complementary oligonucleotide to its complementary sequence in a second oligonucleotide disrupts the hairpin and increases the distance between the two dyes, thus reducing quenching. A disadvantage of the hairpin structure is that it is very stable and conversion to the unquenched, hybridized form is often slow and only moderately favored, resulting in generally poor performance. Tyagi and Kramer (1996. *Nature Biotech.* 14, 303–308) describe a hairpin labeled as described above which comprises a detector sequence in the loop between the self-complementary arms of the hairpin which form the stem. The base-paired stem must melt in order for the detector sequence to hybridize to the target and cause a reduction in quenching. A "double hairpin" probe and methods of using it are described by B. Bagwell, et al. (1994. *Nucl. Acids Res.* 22, 2424–2425; U.S. Pat. No. 5,607,834). These structures contain the target binding sequence within the hairpin and therefore involve competitive hybridization between the target and the self-complementary sequences of the hairpin. Bagwell solves the problem of unfavorable hybridization kinetics by destabilizing the hairpin with mismatches.

Homogeneous methods employing energy transfer or other mechanisms of fluorescence quenching for detection of nucleic acid amplification have also been described. L. G. Lee, et al. (1993. *Nuc. Acids Res.* 21, 3761–3766) disclose a real-time detection method in which a doubly-labeled detector probe is cleaved in a target amplification-specific manner during PCR. The detector probe is hybridized downstream of the amplification primer so that the 5'-3' exonuclease activity of Taq polymerase digests the detector probe, separating two fluorescent dyes which form an energy transfer pair. Fluorescence intensity increases as the probe is cleaved.

Signal primers (sometimes also referred to as detector probes) which hybridize to the target sequence downstream of the hybridization site of the amplification primers have been described for homogeneous detection of nucleic acid amplification (U.S. Pat. No. 5,547,861 which is incorporated herein by reference). The signal primer is extended by the polymerase in a manner similar to extension of the amplification primers. Extension of the amplification primer displaces the extension product of the signal primer in a target amplification-dependent manner, producing a double-stranded secondary amplification product which may be detected as an indication of target amplification. Examples of homogeneous detection methods for use with single-stranded signal primers are described in U.S. Pat. No. 5,550,025 (incorporation of lipophilic dyes and restriction sites) and U.S. Pat. No. 5,593,867 (fluorescence polarization detection). More recently signal primers have been adapted for detection of nucleic acid targets using FET methods. U.S. Pat. No. 5,691,145 discloses G-quartet structures containing donor/quencher dye pairs appended 5' to the target binding sequence of a single-stranded signal primer. Synthesis of the complementary strand during target amplification unfolds the G-quartet, increasing the distance between the donor and quencher dye and resulting in a detectable incease in donor fluorescence. Partially single-stranded, partially double-stranded signal primers labeled with donor/quencher dye pairs have also recently been described. For example, EP 0 878 554 discloses signal primers with donor/quencher dye pairs flanking a single-stranded restriction endonuclease recognition site. In the presence of the target, the restriction site becomes double-stranded and cleavable by the restriction endonuclease. Cleavage separates the dye pair and decreases donor quenching. EP 0 881 302 describes signal primers with an intramolecularly base-paired structure appended thereto. The donor dye of a donor/quencher dye pair linked to the intramolecularly base-paired structure is quenched when the structure is folded, but in the presence of target a sequence complementary to the intramolecularly base-paired structure is synthesized. This unfolds the intramolecularly base-paired structure and separates the donor and quencher dyes, resulting in a decrease in donor quenching. Nazarenko, et al. (U.S. Pat. No. 5,866,336) describe a similar method where in amplification primers are configured with hairpin structures which carry donor/quencher dye pairs.

Energy transfer and other fluorescence quenching detection methods have also been applied to detecting a target sequence by hybridization of a specific probe. Japanese Patent No. 93015439 B discloses methods for measuring polynucleotides by hybridizing the single-stranded target to a single-stranded polynucleotide probe tagged with two labels which form an energy transfer pair. The double-stranded hybrid is cleaved between the labels by a-restriction enzyme and fluorescence of one of the labels is measured. A disadvantage of this method is that the restriction site in the probe must also be present in the target sequence being detected. S. S. Ghosh, et al. (1994. *Nucl. Acids Res.* 22, 3155–3159) describe restriction enzyme catalyzed cleavage of fluorophore-labeled oligonucleotides which are analyzed using fluorescence resonance energy transfer. In these assays, the complementary oligonucleotides are hybridized to produce the double-stranded restriction site, with one of the fluorescent labels linked to each of the two strands.

SUMMARY OF THE INVENTION

The present invention employs a signal primer for detection of nucleic acid target sequences. The signal primer comprises two oligonucleotides and is partially single-stranded and partially double-stranded. The first oligonucleotide is referred to as the adapter oligonucleotide. The adapter oligonucleotide is hybridized to a complementary second oligonucleotide such that the 3' end of the adapter oligonucleotide forms a single-stranded tail region which hybridizes to the target sequence. The portion of the single-stranded 3' tail which hybridizes to the target sequence is referred to as the target binding sequence. The region of the adapter oligonucleotide which is 5' to the target binding sequence and the 3' single-stranded tail hybridizes to the second oligonucleotide to form an intermolecularly base-paired, partially double-stranded signal primer molecule under the selected reaction conditions for hybridization of the signal primer to the target. The sequence of the adapter oligonucleotide to which the second oligonucleotide hybridizes (the 5' adapter sequence) comprises a sequence which does not hybridize to the target. The 5' adapter sequence may be selected such that it is the same in a variety of adapter oligonucleotides with different target binding sequences (i.e., a "universal" 5' adapter sequence). This simplifies detection of a variety of different targets, as described below.

The signal primers of the present invention therefore have the advantage that a single labeled reporter probe (described below) may be used for detection of a variety of different target sequences, because a common 5' adapter sequence for hybridiation to a second oligonucleotide may be appended to different target binding sequences in the adapter oligonucleotide. This simplifies synthesis of reporter probes and reduces the cost involved. Although the adapter oligonucleotides must have varying target binding sequences for recognition of different targets, they are easier and less costly to synthesize than reporter probes because they do not require labeling for use in the present invention.

DETAILED DESCRIPTION OF THE INVENTION

Certain terms used herein are defined as follows:

An amplification primer is a primer for amplification of a target sequence by primer extension. For SDA, the 3' end of the amplification primer (the target binding sequence) hybridizes at the 3' end of the target sequence. The amplification primer comprises a recognition site for a restriction endonuclease near its 5' end. The recognition site is for a restriction endonuclease which will cleave one strand of a DNA duplex when the recognition site is hemimodified ("nicking"), as described in U.S. Pat. No. 5,455,166; U.S. Pat. No. 5,270,184 and EP 0 684 315. A hemimodified recognition site is a double stranded recognition site for a restriction endonuclease in which one strand contains at least one derivatized nucleotide which causes the restriction endonuclease to nick one of the two strands rather than cleave both strands of the recognition site. The amplification primer also comprises a 3'-OH group which is extendible by DNA polymerase when the target binding sequence of the amplification primer is hybridized to the target sequence. For the majority of the SDA reaction, the amplification primer is responsible for exponential amplification of the target sequence.

As no special sequences or structures are required to drive the amplification reaction, amplification primers for PCR may consist only of target binding sequences. Amplification primers for 3SR and NASBA, in contrast comprise an RNA polymerase promoter near the 5' end. The promoter is appended to the target sequence and serves to drive the amplification reaction by directing transcription of multiple RNA copies of the target.

Extension products are nucleic acids which comprise a primer or a portion of a primer and a newly synthesized strand which is the complement of the target sequence downstream of the primer binding site. Extension products result from hybridization of a primer to a target sequence and extension of the primer by polymerase using the target sequence as a template.

The terms target or target sequence refer to nucleic acid sequences to be amplified or detected. These include the original nucleic acid sequence to be amplified, its complementary second strand and either strand of a copy of the original sequence which is produced by replication or amplification. The target sequence may also be referred to as a template for extension of hybridized primers.

A signal primer according to the present invention comprises two oligonucleotides. In the signal primer, the oligonucleotides are hybridized such that the first oligonucleotide (the adapter oligonucleotide) forms a single-stranded 3' "tail" which hybridizes to the target sequence (the target binding sequence). A second oligonucleotide is base-paired (i.e., hybridized) with a 5' adapter sequence in the first oligonucleotide which is adjacent and 5' to the target binding sequence. As used herein, the term "adjacent and 5' to the target binding sequence" means that all or part of the target binding sequence is left single-stranded in the 3' tail and is available for hybridization to the target. That is, a portion of the target binding sequence may be involved in the intermolecular base-pairing of the adjacent double-stranded portion or the entire target binding sequence may form a single-stranded 3' tail in the signal primer. The remainder of the double-stranded portion of the signal primer is not complementary to the target. Mismatches in the intermolecularly base-paired portion of the signal primer may reduce the magnitude of the change in fluorescence in the presence of target but are acceptable if assay sensitivity is not a concern. Mismatches in the target binding sequence of the single-stranded tail are also acceptable and may be used to detect single nucleotide polymorphisms, but may also reduce assay sensitivity and/or specificity under certain circumstances. However, perfect matches in the sequences involved in hybridization improve assay specificity without significant negative effects on reaction kinetics.

In a first embodiment, the second oligonucleotide of the signal primers of the invention is a reporter probe. The reporter probe comprises at least one donor/quencher dye pair, i.e., a fluorescent donor dye and a quencher for the donor fluorophore. The sequence of the reporter probe is selected so that when it is not hybridized to the 5' adapter sequence of the adapter oligonucleotide the reporter probe spontaneously adopts a conformation which brings the donor and quencher dyes into close spatial proximity and results in quenching of donor fluorescence. The reporter probe may fold into an ordered secondary structure (e.g., a G-quartet, hairpin or triple helix), into a random coil or into any other conformation which brings the donor and quencher dyes into close enough proximity to produce fluorescence quenching. When the reporter probe is hybridized to the adapter oligonucleotide, however, it is linearized or unfolded and the members of the donor/quencher dye pair are spatially-separated such that quenching is reduced or eliminated. In the presence of target, the reporter probe is separated from the adapter oligonucleotide and assumes the quenched conformation. The difference in the extent of fluorescence quenching between adapter-hybridized reporter probe and reporter probe which is not hybridized to the adapter oligonucleotide is used as an indicator of the presence or absence of the target to which the signal primer binds through its target binding sequence. In summary, the dyes of the reporter probe are sufficiently separated when the reporter probe is hybridized to the adapter that the donor produces detectable fluorescence and separation of the reporter probe from its complementary sequence in the adapter oligonucleotide results in an increase in fluorescence quenching as folding of the displaced reporter probe brings the donor and quencher into closer spatial proximity.

Alternatively, the reporter probes of the invention need not be hybridized to the adapter oligonucleotide. In a second embodiment, the signal primers of the invention comprise an adapter oligonucleotide hybridized to an unlabeled second oligonucleotide. An unhybridized reporter probe is also present in its folded, quenched conformation. The unlabeled second oligonucleotide and the reporter probe are sufficiently complementary in sequence that they will hybridize under the selected reaction conditions. Target-dependent disruption of the duplex portion of the signal primer with separation of the unlabeled second oligonucleotide allows the now single-stranded unlabeled second oligonucleotide to hybridize with its complementary sequences in the reporter probe. Prior to hybridization with the displaced unlabeled second oligonucleotide, the reporter probe is folded into an ordered secondary structure, random coil or other conformation which brings the donor and quencher dyes into close spatial proximity and increases quenching of the donor. Hybridization to the unlabeled second oligonucleotide linearizes or unfolds the reporter probe such that the distance between the two dyes is increased and fluorescence quenching is decreased. Decreased quenching produces a detectable change in a fluorescence parameter of either the donor or the quencher which may be detected as an indication of the presence of the target sequence. Both members of the dye pair may be linked to sequences in the reporter probe which are involved in hybridization with the displaced unlabeled second oligonucleotide or one member of the dye pair may be linked to a portion of the reporter probe which is not hybridized to the unlabeled second oligonucleotide, for example in a single-stranded tail on the reporter probe or at an internal sequence which is not complementary to the unlabeled second oligonucleotide.

A donor fluorophore and its corresponding quencher may be linked to the reporter probe at any relative positions which do not inhibit its hybridization to the adapter oligonucleotide or to an unlabeled probe (as described below), which result in detectable donor fluorescence when the reporter probe is hybridized to the adapter or to the unlabeled-probe and which provide a change in a fluorescence parameter when the reporter probe changes between the folded and hybridized states. In the embodiment of the invention where the reporter probe is hybridized to the adapter oligonucleotide in the signal primer, target-dependent disruption of the duplex with separation of the base-paired oligonucleotides allows the reporter probe to fold into an ordered secondary structure, random coil or other conformation which brings the donor and quencher dyes into close spatial proximity and increases quenching of the donor. Inceased quenching produces a detectable change in a fluorescence parameter of either the donor or the quencher which may be detected as an indication of the presence of the target sequence. Both members of the dye pair may be linked to sequences involved in formation of the intermolecular hydrogen bonds in the double-stranded portion of the signal primer. Alternatively, one member of the pair may be linked to a portion of the reporter probe which is not hybridized to the adapter, for example in a single-stranded 3' tail on the reporter probe which is complementary to neither the target or to the adapter oligonucleotide.

In general, the overall length of the sequences involved in intermolecular base-pairing between the adapter and either the unlabeled oligonucleotide or the reporter probe, or between the unlabeled second oligonucleotide and the reporter probe, is not critical. The appropriate length is determined by the number of nucleotides required for stable base-pairing to maintain a partially double-stranded molecule under the selected reaction conditions. For convenience, the sequences involved in base-pairing are typically between about 8 and 75 nucleotides in length. The maximum length is limited only by practical concerns such as the case and efficiency of oligonucleotide synthesis and recovery.

The sequence of the double-stranded region of the signal primer is selected such that at least a portion of it is not complementary to the target and such that it is relatively stable at the temperature of the reaction which serves to disrupt it. However, it must not be so stable that hybridization to the target is unacceptably slow or so stable that the polymerase is unable to displace the second oligonucleotide from the adapter oligonucleotide for synthesis of the complementary strand. Preferably, the $T_m$ of the double-stranded portion of the signal primer involving hybridization between the first oligonucleotide and a second oligonucleotide is equal to or greater than the temperature at which the displacement reaction will occur, but it may be lower. If the $T_m$ of this segment is less than the reaction temperature, more than half of the detector nucleic acid molecules will be fully single-stranded independent of the presence of the target. This reduces assay sensitivity but may be acceptable when relatively high quantities of target are present. Typically, the $T_m$ of the double-stranded portion of the signal primer involving hybridization between the first oligonucleotide and a second oligonucleotide is selected to be equal to or up to about 30° C. higher than the temperature of the reaction which displaces the second oligonucleotide. Most preferably, the $T_m$ is about 10–20° C. higher than the reaction which displaces the second oligonucleotide.

The second oligonucleotide (either a reporter probe or an unlabeled second oligonucleotide) is selected such that when it hybridizes to the adapter oligonucleotide a portion of the adapter oligonucleotide remains single-stranded as a 3' "WI". The single-stranded tail portion of the signal primer is complementary to the target sequence to be detected and serves to hybridize the signal primer to the target sequence. The sequence of the tail is preferably selected such that it will form a stable duplex with the target under the selected reaction conditions and provide the desired degree of detection specificity as is known in the art. To favor hybridization to target, the sequence of the single-stranded target binding tail region of the first oligonucleotide is also preferably selected such that the $T_m$ of the target binding sequence/target duplex is equal to or higher than the reaction temperature. Although the sequence of the target binding region is dictated by the sequence of the target to be detected, adjustments in the $T_m$ of the target binding sequence of the detector nucleic acid may be made, for example, by adjusting its length.

The signal primers of the invention may be used as signal primers in amplification reactions to generate secondary amplification products with an accompanying change in a fluorescence parameter, as described in U.S. Pat. No. 5,547, 861. The single-stranded tail of the signal primer, comprising the 3' end of the adapter oligonucleotide, allows for primer extension. The use of signal primers in a nucleic acid amplification reaction according to a first embodiment of the invention is illustrated in more detail in FIG. 1, and may be summarized as follows. In this first embodiment, the second oligonucleotide is a reporter probe which comprises a donor/quencher dye pair linked thereto such that the members of the pair are spatially separated and donor fluorescence is detectable when the reporter probe is hybridized to the adapter. Via the single-stranded tail of the adapter, the signal primer hybridizes to one strand of the target sequence downstream of an amplification primer. Both the amplification primer and the adapter oligonucleotide of the signal primer are extended by DNA polymerase using the target sequence as a template. The first extension product of the signal primer, with the reporter probe still hybridized to it, is displaced from the template by extension of the upstream amplification primer. The signal primer is still partially double-stranded after displacement of the first signal primer extension product from the target. The extended, displaced signal primer in turn serves as a template for hybridization and extension of a second amplification primer, initially rendering the single-stranded portion of the signal primer extension product double-stranded. Further polymerization of a new strand complementary to the adapter also displaces the reporter probe from the adapter due to the strand displacing activity of the polymerase. As the reporter probe comprises a sequence which spontaneously folds into an ordered secondary structure, a random coil or some other conformation which brings the donor and the quencher into close spatial proximity, separation from the adapter oligonucleotide allows such folding to occur. Fluorescence quenching is thereby increased and a change in any appropriate fluorescence parameter associated with a change in the extent of fluorescence quenching may be detected as an indication of amplification of the target sequence.

Figure 1:
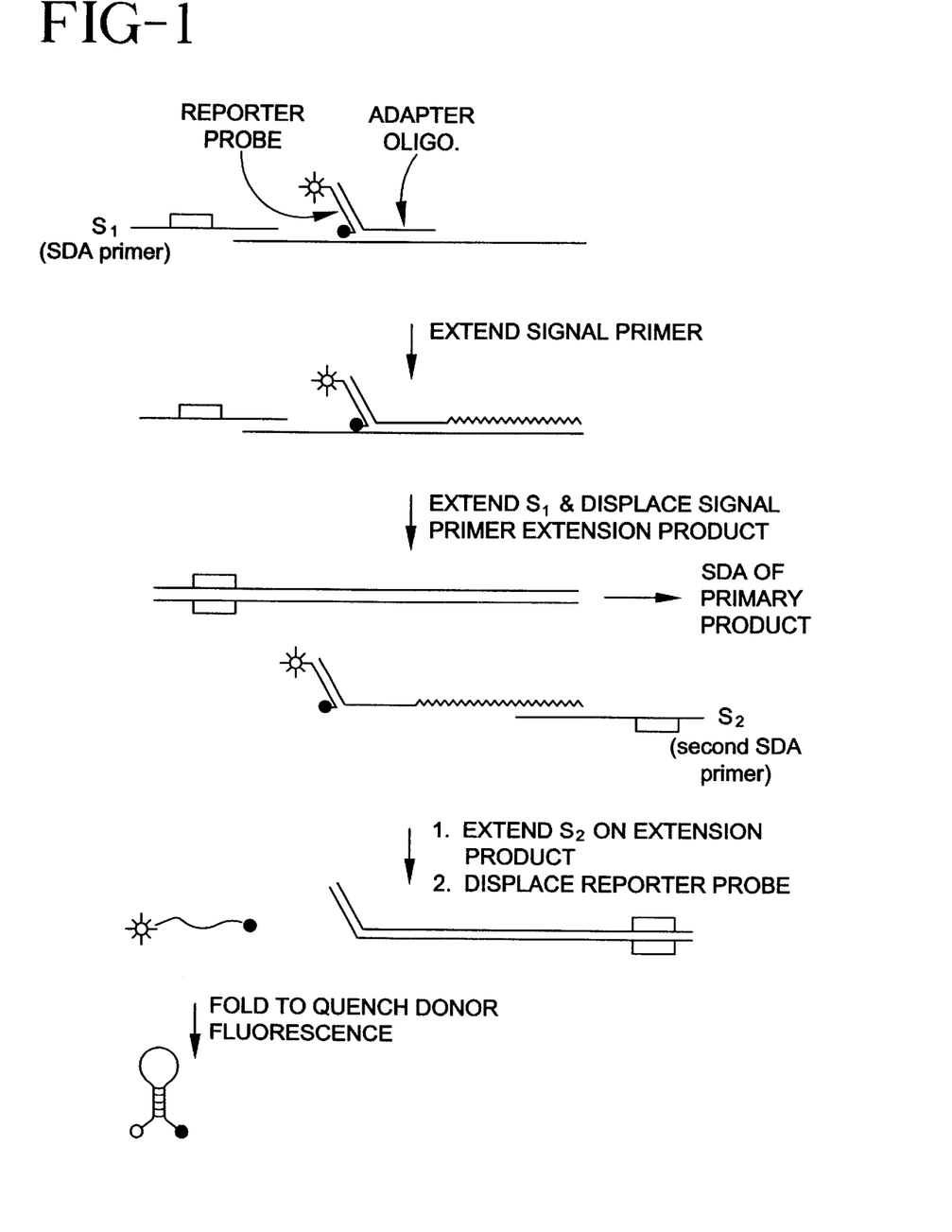
FIG. 1 illustrates detection of a nucleic acid target sequence in a Strand Displacement Amplification (SDA) reaction wherein the second oligonucleotide of the signal primer is a reporter probe.

A second signal primer which hybridizes to the second, complementary strand of a double-stranded target sequence may optionally be included in the reaction. The second signal primer hybridizes to the second strand of the target sequence downstream of the second amplification primer and is extended and displaced by extension of the second amplification primer. The single-stranded portion of the second signal primer extension product is rendered double-stranded by hybridization and extension of the first amplification primer, resulting in displacement of the reporter probe.

Figure 2:
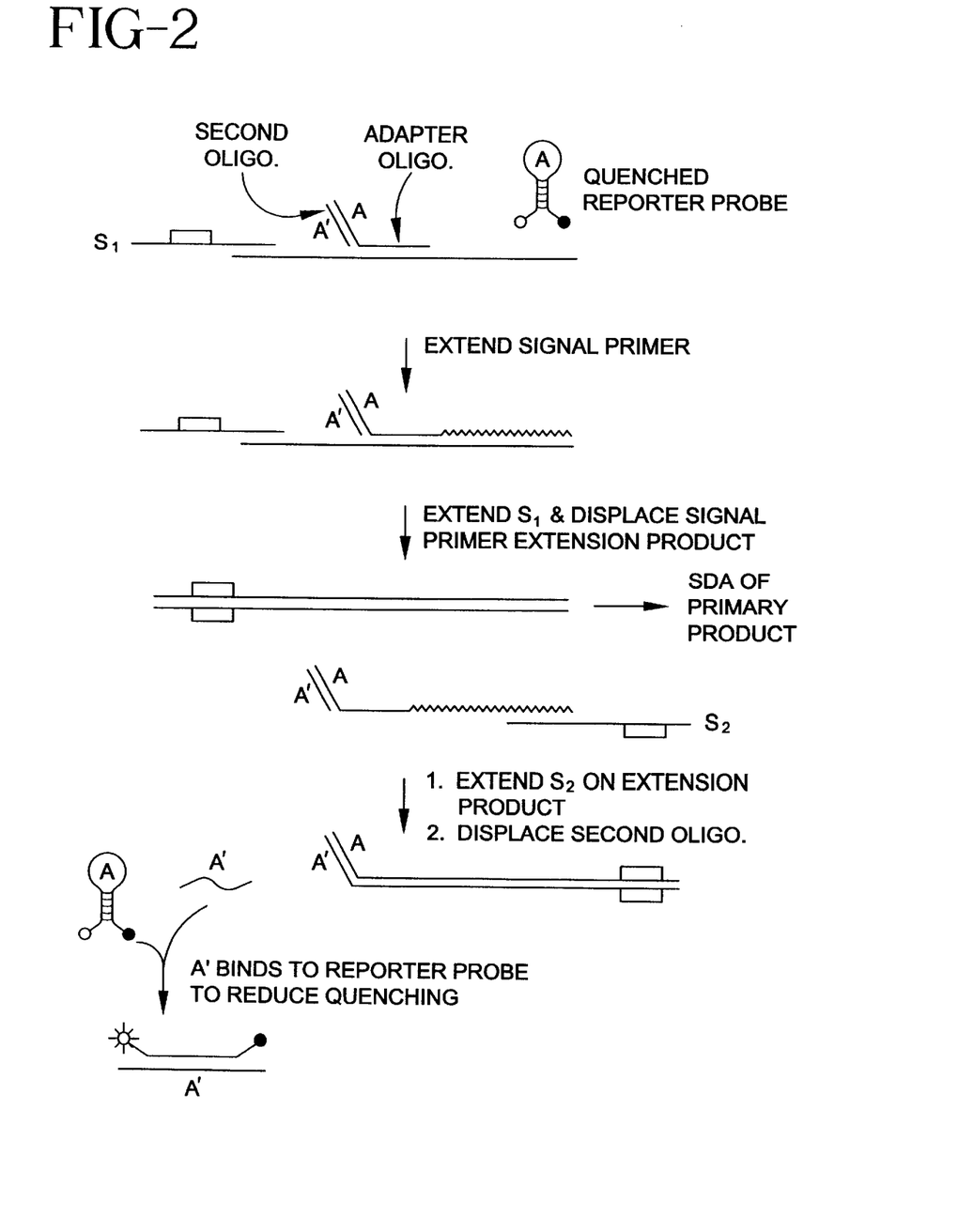
FIG. 2 illustrates detection of a nucleic acid target sequence in an SDA reaction wherein the second oligonucleotide of the signal primer is an unlabeled probe.

The reaction scheme described above and illustrated in FIG. 1 is the same when the second oligonucleotide is unlabeled. However, target-dependent separation of the unlabeled second oligonucleotide from the adapter oligonucleotide is not directly detectable. As shown in FIG. 2, separation of the unlabeled second oligonucleotide from the adapter is detected by hybridization to a reporter probe which is present in its folded, quenched conformation. Hyridization of the unlabeled probe to the complementary reporter probe causes the reporter probe to unfold or linearize, increasing the distance between the donor and quencher dyes and reducing fluorescence quenching. Hybridization between the second oligonucleotide and the reporter probe, which is an indication of the presence of the target, is detected as a change in a fluorescence parameter associated with a change in the extent of fluorescence quenching.

In either embodiment, multiple signal primers per strand of target may be employed if desired, each hybridizing to the target sequence downstream of the other on the same strand, with all signal primers being hybridized downstream of the amplification primer. In this manner, each signal primer is displaced by extension of the upstream detector nucleic acid and the most 5' signal primer is displaced by the amplification primer. Use of multiple signal primers has the advantage of increasing or amplifying the signal generated per target, with an increase in sensitivity of the assay.

Multiple signal primers according to the invention may also be used to simultaneously detect a plurality of different target sequences. In this case, the 5' adapter sequence of the adapter oligonucleotide is preferably different for each target to be detected. By labeling reporter probes specific for the 5' adapter sequence of each target-specific adapter oligonucleotide with donor/quencher dye pairs which are distinguishable, the presence of each target may be determined by detecting changes in the extent of fluorescence quenching in the reporter probe directed to each target.

As shown in FIGS. 1 and 2, the single-stranded portion of the signal primer is converted to double-stranded form by hybridization and extension of an amplification primer. Strand displacement by the polymerase also displaces the reporter probe or unlabeled second oligonucleotide from the adapter oligonucleotide as the polymerase synthesizes its complementary strand. As the strand displacing activity of the polymerase separates a reporter probe from the adapter oligonucleotide, the reporter probe folds and the distance between the donor and quencher dye is decreased, thereby increasing quenching of donor fluorescence. That is, the single-stranded, displaced reporter probe thus produced is free to self-hybridize or otherwise intramolecularly interact to bring the dyes into closer spatial proximity. If the single-stranded, displaced oligonucleotide is an unlabeled second oligonucleotide, it becomes free to hybridize to a reporter probe which is in its folded, quenched state either in solution or attached to a solid phase. Hybridization of the displaced unlabeled second oligonucleotide to the reporter probe at least partially unfolds it, thereby increasing the distance between the donor and the quencher and decreasing quenching of donor fluorescence. In either embodiment, the change in fluorescence of either the donor or quencher dye may be monitored or detected as an indication of amplification of the target sequence. For displacement of a reporter probe, a decrease in donor fluorescence intensity or an increase in quencher fluorescence intensity may be detected and/or monitored as an indication that target amplification is occurring or has occurred. For displacement of an unlabeled second oligonucleotide, an increase in donor fluorescence intensity or a decrease in quencher fluorescence intensity may be detected and/or monitored as an indication that target amplification is occurring or has occurred. Other fluorescence parameters which are affected by the proximity of the donor fluorophore and its quencher (e.g., fluorescence lifetime or a change in a ratio of donor and/or acceptor fluorescence intensities) may also be monitored in either embodiment.

It will be apparent that, in addition to SDA, the signal primers of the invention may be adapted for use as signal primers in other primer extension amplification methods (e.g., PCR, 3SR, TMA or NASBA). For example, the methods may be adapted for use in PCR by using PCR amplification primers and a strand displacing DNA polymerase which lacks 5'→3' exonuclease activity (e.g., Sequencing Grade Taq from Promega or exo⁻ Vent or exo⁻ Deep Vent from New England BioLabs) in the PCR. The signal primers hybridize to the target downstream from the PCR amplification primers. They are extended, displaced from the target and rendered double-stranded with displacement of the reporter probe or unlabeled second oligonucleotide essentially as described for SDA. As in SDA systems, displacement of the reporter probe or unlabeled second oligonucleotide results in a change in the proximity of donor/acceptor dye pairs and changes the level of fluorescence quenching. An associated change in a fluorescence parameter, such as intensity, serves as an indication of target amplification.

For adaptation of the inventive methods to 3SR, TMA or NASBA, a 5'→3' exonuclease deficient reverse transcriptase with strand displacing activity is employed, with hybridization of the signal primer to the RNA target downstream of an amplification primer which contains an RNA polymerase promoter. In a reaction scheme similar to that previously described, the hybridized signal primer comprising the hybridized reporter probe or unlabeled second oligonucleotide is 1) extended, and 2) displaced by extension of the upstream amplification primer. The displaced extension product is then made entirely double-stranded by hybridization and extension of the second amplification primer. This displaces the reporter probe or unlabeled second oligonucleotide from the adapter oligonucleotide of the signal primer, altering the distance between the donor and quencher dyes of a reporter probe and resulting in a change in the level of fluorescence quenching of the donor fluorophore. The signal primer for 3SR or NASBA does not contain an RNA polymerase promoter sequence and therefore cannot function as an amplification primer, reducing nonspecific background signal. This is analogous to the signal primer in SDA, which does not contain a nickable RERS and therefore does not significantly contribute to exponential background amplification of non-specific targets.

For reduced background, it is preferred that the signal primers of the invention be used as described above, with the signal primer extension product being separated from the target sequence by displacement due to extension of the upstream amplification primer. However, it will be apparent that the amplification primers known for use in the various nucleic acid amplification reactions may also be modified by addition of a 5' intermolecularly base-paired sequence as described for the signal primers of the invention. In this embodiment, the amplification primer extension product, with the 5' double-stranded portion, may be separated from the target sequence by displacement due to extension of an upstream non-amplification primer (e.g., bumper primers as in SDA), by denaturation (e.g., heating as in PCR) or by enzymatic digestion of the target strand (e.g., RNase H as in 3SR). Amplification primers comprising the 5' double-stranded portion and the donor/acceptor dye pair eliminate the need for the additional signal primer in the reaction, but because background may be higher in this embodiment the sensitivity of the assay may be decreased.

For PCR, the amplification primer is modified to be an adapter oligonucleotide by addition of sequences 5' to the target binding sequence which are complementary to the reporter probe or unlabeled second oligonucleotide. The reporter probe or unlabeled second oligonucleotide is then hybridized to the added 5' sequence. This primer is structurally identical to the PCR signal primer described above. Functionally, however, it is different in that there is no downstream primer to be extended and displaced and the amplification primer itself provides the change in fluorescence. For 3SR, NASBA and TMA, the sequence complementary to the second oligonucleotide may be placed 5' to the promoter of an amplification primer and the second oligonucleotide hybridized to it so that the second oligonucleotide is displaced and the adapter oligonucleotide is rendered totally double-stranded in the double-stranded DNA portion of the amplification cycle. A second amplification primer which does not contain a promoter sequence (e.g., as in NASBA) may also or alternatively contain the sequences complementary to the hybridized second oligonucleotide 5' to the target binding sequence.

In another alternative embodiment, the signal primers of the invention may be used in non-amplification based assay formats to detect target oligonucleotides. In a first non-amplification embodiment, the 3' single-stranded target binding sequence of the adapter hybridizes to the 3' end of the target oligonucleotide such that the base-paired duplex portion of the signal primer forms a 5' overhang. The target sequence functions as a primer in a primer extension reaction to synthesize a strand complementary to the adapter oligonucleotide using a strand displacing polymerase which extends the target sequence using the 5' overhang (i.e., the sequence of the adapter which is base-paired to the second oligonucleotide) as a template. If the target binding sequence of the detector nucleic acid hybridizes to only a portion of the target sequence, the target sequence also forms a 5' overhang and the adapter oligonucleotide of the signal primer is similarly extended using the 5' overhang of the target as a template. If the target binding sequence of the signal primer is complementary to the entire length of the target sequence only the target is extended. In either case, the second oligonucleotide of the signal primer is thus displaced from the adapter with an accompanying change in a fluorescence parameter as described above. Extension with displacement of the second oligonucleotide to produce a change in fluorescence can take place only in the presence of target.

It is a feature of the invention that the target is not initially required to hybridize to the base-paired sequences in the detector nucleic acid. In many prior art assays, initial competitive hybridization reduces the affinity of a probe or primer for the target and decreases assay sensitivity. In contrast, the initial non-competitive binding of the signal primers of the invention better favors intermolecular hybridization in any subsequent competitive hybridization reaction. The length of the single-stranded 3' tail may be adjusted without affecting the thermodynamic properties of the duplex portion of the signal primer, so target hybridization may be optimized without requiring redesign of the duplex portion of the signal primer. This greatly simplifies primer design as compared to the prior art.

The change in fluorescence resulting from displacement of the reporter probe or unlabeled second oligonucleotide may be detected at a selected endpoint in the reaction. However, because completely or partially displaced second oligonucleotides are produced concurrently with hybridization and primer extension, the change in fluorescence may also be monitored as the reaction is occurring, i.e., in "real-time". This homogeneous, real-time assay format can be used to provide semi-quantitative or quantitative information about the initial amount of target present. For example, the rate at which fluorescence intensity changes during the second oligonucleotide displacement reaction (either as part of target amplification or in non-amplification detection methods) is an indication of initial target levels. As a result, when more initial copies of the target sequence are present, fluorescence more rapidly reaches a selected threshold value (i.e., shorter time to positivity). In addition, the rate of change in fluorescence parameters during the course of the second oligonucleotide displacement reaction is more rapid in samples containing higher initial amounts of target than in samples containing lower initial amounts of target. These or other measurements as are known in the art may be made as an indication of the presence of target or as an indication of target amplification. The initial amount of target is typically determined by comparison of the experimental results to results for known amounts of target.

Many donor/quencher dye pairs known in the art are useful in the present invention. These include, for example, fluorescein isothiocyanate (FITC)/tetramethylrhodamine isothiocyanate (TRITC), FITC/Texas Red™ (Molecular Probes), FITC/N-hydroxysuccinimidyl 1-pyrenebutyrate (PYB), FITC/eosin isothiocyanate (EITC), N-Docket hydroxysuccinimidyl 1-pyrenesulfonate (PYS)/FITC, FITC/Rhodamine X, FITC/tetramethylrhodamine (TAMRA), and others. The selection of a particular donor/quencher pair is not critical. For energy transfer quenching mechanisms it is only necessary that the emission wavelengths of the donor fluorophore overlap the excitation wavelengths of the quencher, i.e., there must be sufficient spectral overlap between the two dyes to allow efficient energy transfer, charge transfer or fluorescence quenching. P-(dimethyl aminophenylazo) benzoic acid (DABCYL) is a non-fluorescent quencher dye which effectively quenches fluorescence from an adjacent fluorophore, e.g., fluorescein or 5-(2'-aminoethyl) aminonaphthalene (EDANS). Certain donor/quencher pairs are exemplified above and in the following Examples, however, others will be apparent to those skilled in the art and are also useful in the invention. Any dye pair which produces fluorescence quenching in the detector nucleic acids of the invention are suitable for use in the methods of the invention, regardless of the mechanism by which quenching occurs. Terminal and internal-labeling methods are also known in the art and may be routinely used to link the donor and quencher dyes at their respective sites in the detector nucleic acid.

EXAMPLE 1

Strand Displacement Amplification reactions containing signal primers according to the invention were run essentially as described in U.S. Pat. No. 5,547,861 for detection of a synthetic target sequence. A first reaction contained 106 copies of the target sequence SDA amplification primers appropriate for amplification of the synthetic target sequence, and a signal primer (UDP1) according to the invention comprising an adapter oligonucleotide having a target binding sequence specific for the target and a 5' sequence complementary to a reporter probe, and a reporter probe labeled with fluorescein and dabcyl. The sequence of the reporter probe was selected such that when not hybridized to its complementary sequence it would spontaneously fold into a hairpin structure, bringing the two dyes into closer spatial proximity and increasing fluorescence quenching as compared to the extent of fluorescence quenching when the reporter probe was hybridized to a complementary sequence. The sequences of the signal primer (shown in the 5' to 3' direction) were as follows. The target binding sequence of the adapter oligonucleotide is shown in italics and the complementary sequences in the adapter oligonucleotide and the reporter probe are underlined. The 5' and 3' sequences of the reporter probe hybridize to form a hairpin.

Figure 3:
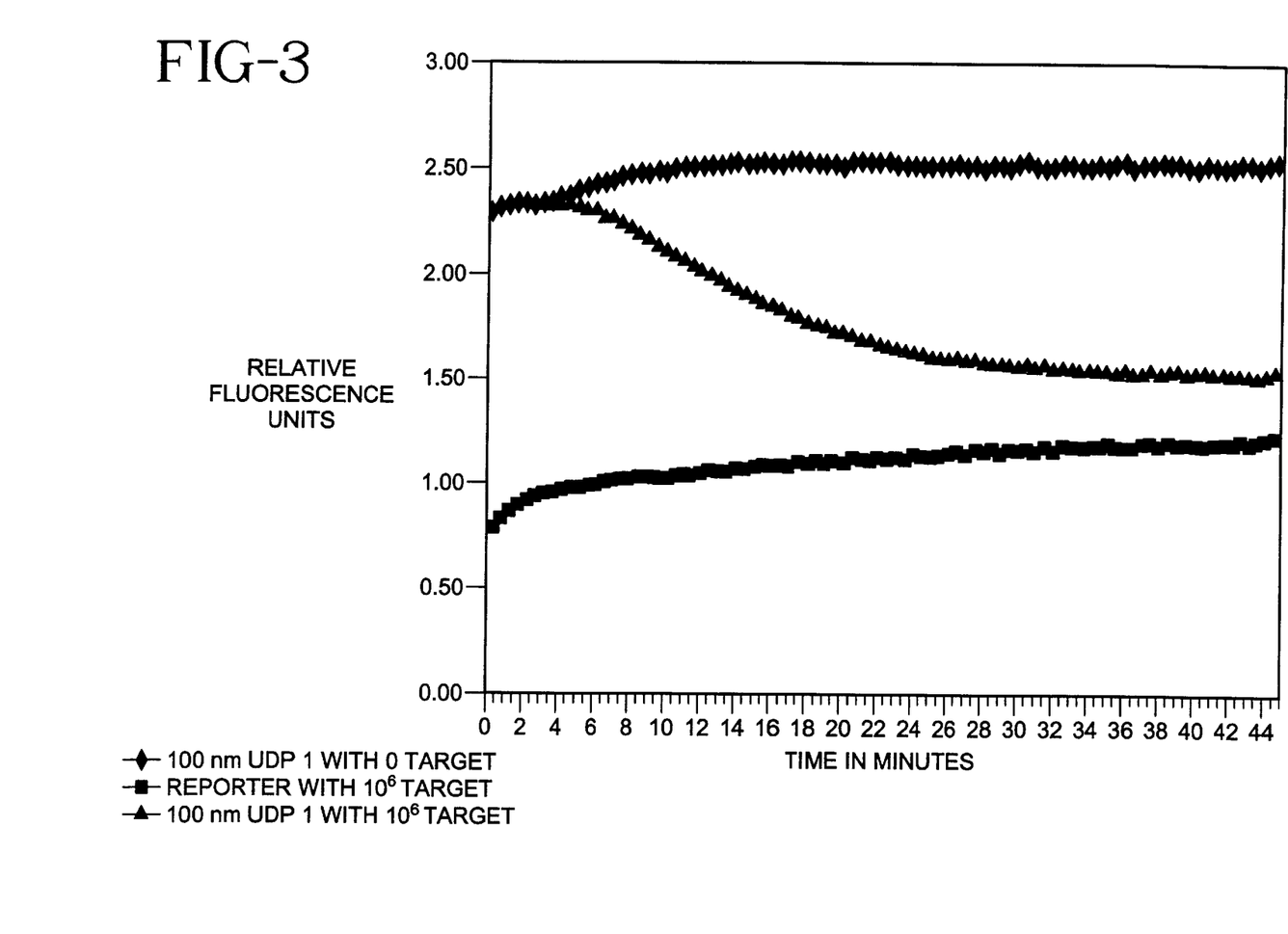
FIG. 3 shows the results of Example 1, using a reporter probe comprising a sequence which spontaneously forms a hairpin structure when not hybridized to a complementary sequence.

Adapter Oligonucleotide (SEQ ID NO:1):
  TCGGGTGGCTCCTTCTGATAATGACT-CACTGAGCTGGAACGTCGT Reporter Probe (SEQ ID NO:2):
  fluorescein-CAGCATTATCAGAAGGAGCCACCCGATAATG CTG-dabcyl A second reaction contained no target and the same signal primer as in the first reaction. A third reaction was a control reaction which contained $10^6$ copies of target and reporter probe only (i.e., no adapter oligonucleotide). Fluorescein fluorescence intensity of was detected in real-time during the amplification reactions. As shown in FIG. 3, in the absence of target donor fluorescence remained high (relatively unquenched) throughout the reaction indicating that the reporter probe was not displaced from the adapter oligonucleotide in the signal primer. In the presence of target, however, donor fluorescence was initially high (relatively unquenched) but decreased during the time course of the amplification reaction as reporter probe was displaced and assumed its relatively more quenched conformation. In the absence of signal primer donor fluorescence remained quenched throughout the amplification reaction. These results demonstrate that the signal primers of the invention can be used to detect a nucleic acid target sequence by monitoring changes in the extent of fluorescence quenching.

EXAMPLE 2

Example 1 was repeated using a reporter probe sequence (UDP5) which when not hybridized to its complement spontaneously forms a G-quarter structure which brings the donor and quencher dyes into closer spatial proximity than when the reporter probe is hybridized to a complementary sequence. The adapter oligonucleotide and reporter probe sequences are shown below. The entire sequence of the reporter probe is incorporated in the G-quartet when the reporter probe is not hybridized to a complementary sequence.

Adapter Oligonucleotide (SEQ ID NO:3):

CCCAAAACCCAAAACCCAAAACCCACT-CACTGAGCTGGAACGTCGT

Reporter Probe (SEQ ID NO:4):

fluorescein-GGGTTTTGGGTTTTGGGTTTTGGG-dabcyl

Figure 4:
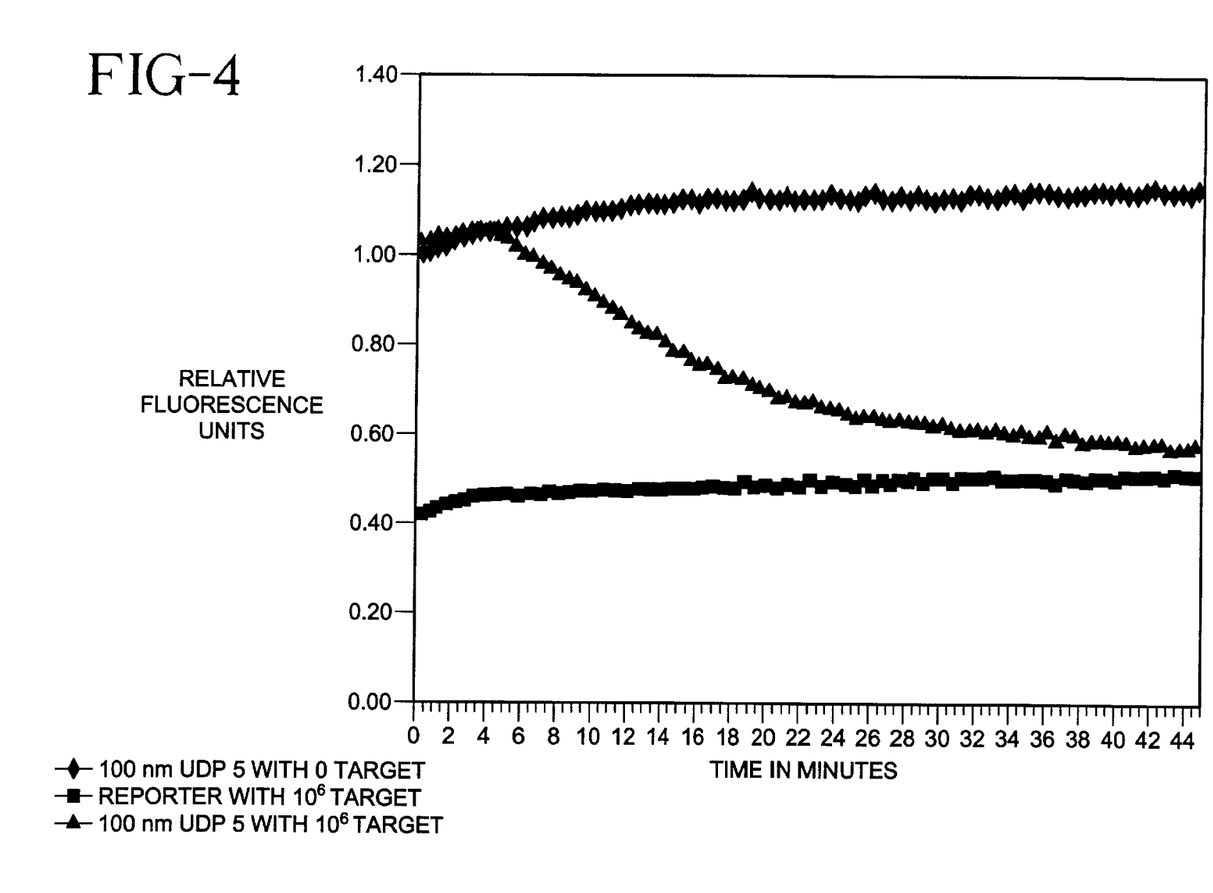
FIG. 4 shows the results of Example 2, using a reporter probe comprising a sequence which spontaneously forms a G-quartet when not hybridized to a complementary sequence.

Again, target amplification resulted in decreased donor fluorescence as the reporter probe was displaced from the adapter oligonucleotide of the signal primer. The reporter probe alone did not recognize the target and no change in donor fluorescence was observed when no target was present. These results are shown in FIG. 4.

What is claimed is:

1. A method for detecting the presence of a nucleic acid target sequence comprising:
   a) hybridizing to the target sequence a signal primer comprising
      i) a reporter probe which in the absence of hybridization to a complementary sequence assumes a conformational structure which brings a fluorescent donor/quencher dye pair linked thereto into sufficiently close spatial proximity to quench donor fluorescence, and,
      ii) an adapter oligonucleotide hybridized to the reporter probe such that the signal primer comprises an intermolecularly base-paired portion and a single-stranded target binding sequence,
   wherein quenching of donor fluorescence in the absence of hybridization of the adapter oligonucleotide and the reporter probe is greater than quenching of donor fluorescence when the adapter oligonucleotide and the reporter probe are hybridized;
   b) in a primer extension reaction, synthesizing a strand complementary to the adapter oligonucleotide, whereby the reporter probe is separated from the adapter oligonucleotide and quenching of donor fluorescence is increased, and;
   c) detecting a change in a fluorescence parameter associated with increased quenching as an indication of the presence of the target sequence.

2. The method of claim 1 wherein the complementary strand is synthesized in a target amplification reaction.

3. The method of claim 1 wherein the complementary strand is synthesized by extension of the target sequence using the adapter oligonucleotide as a template.

4. The method of claim 1 wherein a change in fluorescence intensity is detected as an indication of the presence of the target sequence.

5. The method of claim 4 wherein an increase in donor fluorescence intensity or a decrease in quencher fluorescence intensity is detected as an indication of the presence of the target sequence.

6. The method of claim 1 wherein a change in fluorescence lifetime is detected as an indication of the presence of the target sequence.

7. The method of claim 1 wherein the change in the fluorescence parameter is detected in real-time.

8. The method of claim 1 wherein the change in the fluorescence parameter is detected at an endpoint.

9. The method of claim 1 wherein the fluorescent donor/acceptor dye pair comprises fluorescein and Rhodamine X, Rhodamine X and Cy5, or fluorescein and Dabcyl.

10. A method for detecting amplification of a target sequence comprising, in an amplification reaction:
    a) hybridizing to the target sequence a signal primer comprising
       i) a reporter probe which in the absence of hybridization to a complementary sequence assumes a conformational structure which brings a fluorescent donor/quencher dye pair linked thereto into sufficiently close spatial proximity to quench donor fluorescence, and,
       ii) an adapter oligonucleotide hybridized to the reporter probe such that the signal primer comprises an intermolecularly base-paired portion and a single-stranded target binding sequence,
    wherein quenching of donor fluorescence is greater in the absence of hybridization of the adapter oligonucleotide and the reporter probe than when the adapter oligonucleotide and the reporter probe are hybridized;
    b) extending the adapter oligonucleotide on the target sequence with a polymerase to produce an extension product and separating the extension product from the target sequence;
    c) hybridizing an amplification primer to the extension product and extending the amplification primer with the polymerase, whereby the reporter probe is separated from the adapter oligonucleotide and quenching of donor fluorescence is increased, and;
    d) detecting a change in a fluorescence parameter associated with increased quenching as an indication of amplification of the target sequence.

11. The method of claim 10 wherein the target sequence is amplified by Strand Displacement Amplification, the Polymerase Chain Reaction, 3SR, TMA or NASBA.

12. The method of claim 10 wherein a change in fluorescence intensity is detected.

13. The method of claim 12 wherein the change in fluorescence intensity is detected in real-time.

14. The method of claim 12 wherein the change in fluorescence intensity is detected at a selected end-point in the amplification reaction.

15. The method of claim 10 wherein the fluorescent donor/quencher dye pair comprises fluorescein and Rhodamine X, Rhodamine X and Cy5, or fluorescein and Dabcyl.

16. The method of claim 10 wherein the intermolecularly base-paired portion of the detector nucleic acid comprises a portion of the target binding sequence.

17. A method for detecting the presence of a nucleic acid target sequence comprising:
    a) hybridizing to the target sequence a signal primer comprising a first oligonucleotide hybridized to a second oligonucleotide such that the signal primer comprises an intermolecularly base-paired portion and a single-stranded target binding sequence;
    b) in a primer extension reaction, synthesizing a strand complementary to the first oligonucleotide, whereby the second oligonucleotide is separated from the first oligonucleotide;
    c) hybridizing the separated second oligonucleotide to a reporter probe which in the absence of hybridization to a complementary sequence assumes a conformational structure which brings a fluorescent donor/quencher dye pair linked thereto into sufficiently close spatial proximity to quench donor fluorescence, and wherein quenching of donor fluorescence when the reporter probe and the second oligonucleotide are hybridized is less than quenching of donor fluorescence in the absence of hybridization of the reporter probe and the second oligonucleotide, and;
    d) detecting a change in a fluorescence parameter associated with decreased quenching as an indication of the presence of the target sequence.

18. The method of claim 17 wherein the complementary strand is synthesized in a target amplification reaction.

19. The method of claim 17 wherein the complementary strand is synthesized by extension of the target sequence using the first oligonucleotide as a template.

20. The method of claim 17 wherein a change in fluorescence intensity is detected as an indication of the presence of the target sequence.

21. The method of claim 20 wherein an increase in donor fluorescence intensity or a decrease in quencher fluorescence intensity is detected as an indication of the presence of the target sequence.

22. The method of claim 17 wherein a change in fluorescence lifetime is detected as an indication of the presence of the target sequence.

23. The method of claim 17 wherein the change in the fluorescence parameter is detected in real-time.

24. The method of claim 17 wherein the change in the fluorescence parameter is detected at an endpoint.

25. The method of claim 17 wherein the fluorescent donor/acceptor dye pair comprises fluorescein and Rhodamine X, Rhodamine X and Cy5, or fluorescein and Dabcyl.

26. A method for detecting a nucleic acid target sequence comprising:
   a) hybridizing a signal primer to the target sequence, the signal primer comprising a reporter probe which forms a secondary structure when not hybridized to a complementary sequence and an adapter oligonucleotide hybridized to the reporter probe such that formation of the secondary structure is substantially prevented;
   b) separating the reporter probe from the adapter oligonucleotide in a target-dependent manner, and;
   c) detecting formation of the secondary structure as an indication of the presence of the target sequence.

27. The method of claim 26 wherein the reporter probe is separated from the adapter oligonucleotide in a target amplification reaction.

28. The method of claim 26 wherein formation of the secondary structure is detected by a change in fluorescence.

29. The method of claim 28 wherein the reporter probe is labeled with a donor/quencher dye pair and formation of the secondary structure is detected by an decrease in donor fluorescence.

30. The method of claim 26 wherein the secondary structure is selected from the group consisting of hairpins, G-quartets, triple helices and random coils.

31. The method of claim 26 wherein the adapter oligonucleotide of the signal primer comprises an adapter sequence for hybridization to the reporter probe which is substantially identical to an adapter sequence of a second adapter oligonucleotide of a second signal primer for detection of a second target sequence.

32. A method for detecting a nucleic acid target sequence comprising:
   a) hybridizing a signal primer to the target sequence, the signal primer comprising an adapter oligonucleotide hybridized to a second oligonucleotide, wherein the second oligonucleotide is complementary to a reporter probe which forms a secondary structure when not hybridized to a complementary sequence;
   b) separating the second oligonucleotide from the adapter oligonucleotide in a target-dependent manner, and;
   c) detecting hybridization of the second oligonucleotide to the reporter probe as an indication of the presence of the target sequence.

33. The method of claim 32 wherein the second oligonucleotide is separated from the first oligonucleotide in a target amplification reaction.

34. The method of claim 32 wherein hybridization of the second oligonucleotide to the reporter probe is detected by a change in fluorescence.

35. The method of claim 34 wherein the reporter probe is labeled with a donor/quencher dye pair and hybridization to the second oligonucleotide is detected by an increase in donor fluorescence.

36. The method of claim 32 wherein the secondary structure is selected from the group consisting of hairpins, G-quartets, triple helices and random coils.

37. The method of claim 32 wherein the adapter oligonucleotide of the signal primer comprises an adapter sequence for hybridization to the second oligonucleotide which is substantially identical to an adapter sequence of a second adapter oligonucleotide of a second signal primer for detection of a second target sequence.

* * * * *

SEQUENCE LISTING

<160> NUMBER OF SEQ ID NOS: 4

<210> SEQ ID NO 1
<211> LENGTH: 45
<212> TYPE: DNA
<213> ORGANISM: Artificial Sequence
<220> FEATURE:
<223> OTHER INFORMATION: Description of Artificial Sequence:
      hypothetical synthetic sequence for purposes of examples

<400> SEQUENCE: 1
tcgggtggct ccttctgata atgactcact gagctggaac gtcgt                    45

<210> SEQ ID NO 2
<211> LENGTH: 34
<212> TYPE: DNA
<213> ORGANISM: Artificial Sequence
<220> FEATURE:
<223> OTHER INFORMATION: Description of Artificial Sequence:
      hypothetical synthetic sequence for purposes of examples

<400> SEQUENCE: 2
cagcattatc agaaggagcc acccgataat gctg                                34

<210> SEQ ID NO 3
<211> LENGTH: 46
<212> TYPE: DNA
<213> ORGANISM: Artificial Sequence
<220> FEATURE:
<223> OTHER INFORMATION: Description of Artificial Sequence:
      hypothetical synthetic sequence for purposes of examples

<400> SEQUENCE: 3
cccaaaaccc aaaacccaaa acccactcac tgagctggaa cgtcgt                   46

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence:
      hypothetical synthetic sequence for purposes of examples

<400> SEQUENCE: 4
gggttttggg ttttgggttt tggg                                           24